United States Patent [19]
Miller

[11] Patent Number: 6,027,495
[45] Date of Patent: *Feb. 22, 2000

[54] METHOD AND APPARATUS FOR DERMATOLOGY TREATMENT

[75] Inventor: Iain D. Miller, Charlestown, Mass.

[73] Assignee: Esc Medical Systems Ltd., Israel

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/821,102

[22] Filed: Mar. 20, 1997

Related U.S. Application Data

[63] Continuation of application No. 08/650,843, May 20, 1996, Pat. No. 5,879,376, which is a continuation-in-part of application No. 08/546,791, Oct. 23, 1995, Pat. No. 5,658,323.

[51] Int. Cl.[7] .................................................. A61B 17/36
[52] U.S. Cl. .................................................. 606/9; 607/89
[58] Field of Search .............................. 607/88–89, 96; 606/3, 9, 10, 13, 15

[56] References Cited

U.S. PATENT DOCUMENTS

| | | | |
|---|---|---|---|
| 3,538,919 | 11/1970 | Meyer | 128/398 |
| 3,693,623 | 9/1972 | Harte et al. | 128/303.1 |
| 3,834,391 | 9/1974 | Block | 128/303.1 |
| 4,388,924 | 6/1983 | Weissmann et al. | 128/303.1 |
| 4,564,011 | 1/1986 | Goldman | 128/303.1 |
| 4,617,926 | 10/1986 | Sutton | 128/303.1 |
| 4,733,660 | 3/1988 | Itzkan | 128/303.1 |
| 4,829,262 | 5/1989 | Furumoto | 330/4.3 |
| 4,836,203 | 6/1989 | Müller et al. | 128/203.1 |
| 4,854,320 | 8/1989 | Dew et al. | 128/397 |
| 4,917,084 | 4/1990 | Sinofsky | 606/7 |
| 4,930,504 | 6/1990 | Diamantopoulos et al. | |
| 5,059,192 | 10/1991 | Zalas | 606/9 |
| 5,217,455 | 6/1993 | Tan | |
| 5,226,907 | 7/1993 | Tankovich | 606/133 |
| 5,258,989 | 11/1993 | Raven | 372/6 |
| 5,259,380 | 11/1993 | Mendes et al. | 607/115 |
| 5,282,797 | 2/1994 | Chess | 606/9 |
| 5,290,273 | 3/1994 | Tan | 606/9 |
| 5,304,170 | 4/1994 | Green | 606/9 |
| 5,330,517 | 7/1994 | Mordon et al. | 607/89 |
| 5,334,191 | 8/1994 | Poppas et al. | 606/12 |
| 5,344,418 | 9/1994 | Ghaffari | |
| 5,405,368 | 4/1995 | Eckhouse | 607/88 |
| 5,425,728 | 6/1995 | Tankovich | 606/9 |
| 5,474,549 | 12/1995 | Ortiz et al. | 606/9 |
| 5,522,813 | 6/1996 | Trelles | 606/2 |
| 5,527,350 | 6/1996 | Grove et al. | 607/89 |
| 5,558,667 | 9/1996 | Yarborough et al. | 606/9 |
| 5,611,795 | 3/1997 | Slatkine et al. | |
| 5,658,323 | 8/1997 | Miller | |
| 5,707,403 | 1/1998 | Grove et al. | 607/89 X |
| 5,879,376 | 3/1999 | Miller | 606/9 X |

OTHER PUBLICATIONS

Advertisement for Market Study entitled "Laser–Based Hair Removal" by Michael Moretti & Iain Miller of Medical Insight, Inc., Publication date: (Feb. 1996).

Anderson and Parrish, "The Optics of Human Skin," *The Journal of Investigative Dermatology*, vol. 77, No. 1, 13–19 (1981).

(List continued on next page.)

*Primary Examiner*—John P. Lacyk
*Assistant Examiner*—Ryan Carter
*Attorney, Agent, or Firm*—Eitan, Pearl, Latzer & Cohen-Zedek

[57] ABSTRACT

A laser treatment method is provided which removes vascular and pigmented lesions from the skin of a living human. The methodology involves a carefully designed treatment protocol utilizing a modified optical apparatus. The apparatus is a modified diode laser system, designed for optimal therapeutic selectivity.

21 Claims, 4 Drawing Sheets

OTHER PUBLICATIONS

Anderson and Parrish, "Selective Photothermolysis: precise microsurgery by selective absorption of pulsed radiation" *Science* 220, 524–527 (1983).

Balles et al., "Semiconductor Diode Laser Photocoagulation in Retinal Vascular Disease," *Ophthalmology,* vol. 97, No. 11, 1553–1561 (1990).

Duffy, "Small Vessel Sclerotherapy: An Overview," *Adv. Dermatol.,* vol. 3, 221–242 (1988).

Garden et al., "The Pulsed Dye Laser: Its Use at 577 nm Wavelength," *J. Dermatol. Surg. Oncol.,* vol. 13, No. 2, 134–138 (1987).

Goldman et al., "Continuing medical education (Dermatologic surgery)," *Journal of the American Academy of Dermatology,* vol. 17, No. 2, part 1, 167–184 (1987).

Goldman et al., "Pulsed–Dye Laser Treatment of Leg Telangiectasia: With and Without Simultaneous Sclerotherapy," *J. Dermatol. Surg. Oncol.,* vol. 16, No. 4, 338–344 (1990).

Miller, "Lasers in Plastic Surgery" PhD thesis, University of Strathclyde, Glasgow, Scotland, 1990 (abstract).

Press Release, Carried by Business Wire, Authored by Palomar Medical Technologies, Inc. (Sep. 8, 1995).

"Photosclerosis of cutaneous vascular malformations with a pulsed 810 nm diode laser" by Lawrence S. Bass of Columbia University College of Physicians & Surgeons, New York, NY *SPIE* 2395, 559–565 (Apr., 1995).

METHOD AND APPARATUS FOR DERMATOLOGY TREATMENT

RELATED APPLICATIONS

This application is a continuation-application of Ser. No. 08/650,843 filed May 20, 1996, now U.S. Pat. No. 5,879,376 which in turn is a continuation-in-part of Ser. No. 08/546,791 filed on Oct. 23, 1995 now U.S. Pat. No. 5,658,323. The contents of all of the aforementioned application(s) are hereby incorporated by reference.

FIELD OF THE INVENTION

The present invention is directed to the removal of vascular and other pigmented lesions from the skin utilizing a modified high power diode laser system under carefully controlled conditions.

BACKGROUND

Human skin may contain a range of abnormalities including vascular and pigmented lesions. Although not always dangerous to the individual, such abnormalities are frequently cosmetically troublesome.

Vascular lesions, in particular, may take several manifestations. Common examples are 'port wine' stain birthmarks; telangiectasias (spots or vessel lines formed by dilated capillaries or other small blood vessels); and hemangiomas (benign tumors composed of well-formed blood vessels). Pigmented lesions generally consist of hyperactive melanocytes which produce a local overabundance of melanin.

Leg telangiectasia, or 'leg veins', are chronically dilated blood vessels visually apparent as red or blue linear or 'spider' structures. They may cover extensive or local areas of the leg and are more common in women. Large diameter vessels may cause discomfort, while smaller diameter vessels are more often considered cosmetically unsightly by patients.

Up to 80 million adults in the United States alone are affected by leg veins. It is estimated that 29–41% of women and 6–15% of men worldwide have 'abnormal' (visually apparent) leg veins. Most vessels presenting for treatment are less than 1 mm in diameter although candidates for treatment have diameters up to 3 mm.

The vessels consist of dilated blood channels in an otherwise normal dermal stroma. The blood channels have a single endothelial cell lining with thickened walls consisting of collagen and muscle fibers. Clinically, these vessels may be categorized as linear, arborizing, spider or papular.

Such dilated vessels may result from pregnancy or the use of progestational agents. A genetic link is usually also present. Some such veins are associated with a high pressure flow from a feeding reticular or varicose vein.

In order to eradicate a leg vein, it is usual to damage the endothelial vessel lining or surgically ligate the vessels. Such surgery is radical and performed on an in-patient basis. Endothelial damage may be induced by means of Sclerotherapy or by the use of light energy on an outpatient basis.

Sclerotherapy is currently the favored method of non-surgical leg vein eradication.

Sclerosing agents have traditionally been employed to damage endothelial cells. Such agents as sodium tetradecyl sulfate, hypertonic saline and polidocanol are injected into large vessels (>1 mm in diameter) and result in death of the endothelium. Several systemic injections to a 'feeder' vessel system may result in widespread death of the ectatic vessels.

The use of sclerosing agents is associated with telangiectatic matting (formation of clusters of small vessels) in 35% of patients treated, and with hyperpigmentation (residual brown pigmentary staining) in up to 30% of vessels treated. Other adverse sequelae are possible, including ulceration, edema (blistering) and systemic anaphylactic shock. Vessel recurrence within 5 years has been observed in up to 40% of patients studied. Further, many patients are fearful and resistant to the use of needles.

Hyperpigmentation pursuant to sclerotherapy is particularly troublesome, as it replaces the blue vessels with a brown discoloration which may persist for up to 5 years. This effect results from the catabolism of extravasated blood to hemosiderin, a form of iron deposition, brown in color, which may reside in the proximal dermis for up to 6 months.

Sclerotherapy injection difficulties render sclerotherapy relatively unsuitable for the routine treatment of vessels with diameters of less than 1.0 mm and for the treatment of many larger vessels with diameter in the range 1.0–3.0 mm.

Light energy has been utilized for the treatment of cutaneous vasculature.

When use of light is under consideration, one can choose to vary wavelength, pulsewidth or coherence (uniformity). Wavelength will typically be chosen by consideration of the absorption and scattering characteristics of the target tissue layers. The absorption characteristics are typified by several peaks in the visible region of the spectrum, due to target chromophores, together with a monotonic decrease into the infra-red region. The scattering of tissue decreases monotonically through the visible to the near infra-red region and beyond.

Figure 1:
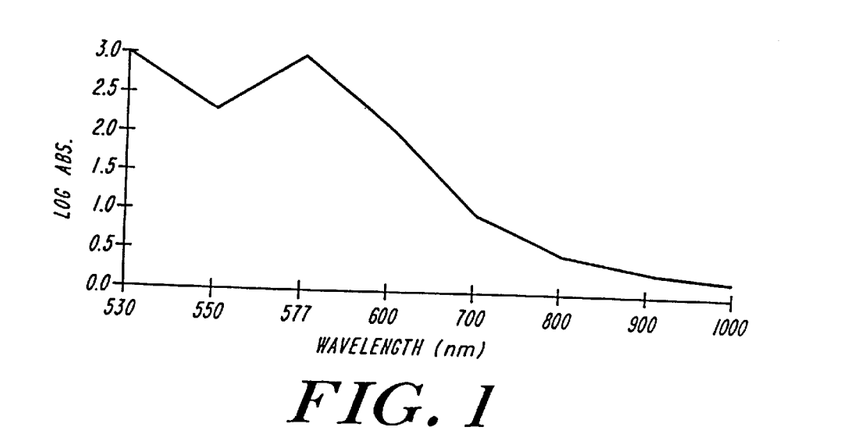

Both coherent laser light and incoherent light from a flashlamp-type source offer the potential for high selectivity of treatment. Short wavelength (<500 nm) light is usually not employed, since it is highly scattered in tissue and therefore unable to penetrate to a sufficient depth. Light of a wavelength greater than 500 nm has been employed for the treatment of vascular lesions. The absorption profile of whole blood is shown in FIG. 1. This profile will vary with anatomical location, since blood constitution varies, but can be taken as generally representative.

Vascular diseases characterised by small vessels such as the Port Wine Stain respond well to visible wavelength pulsed laser light from a pulsed dye laser, typically with a wavelength in the 550–600 nm range, which is tuned to a local absorption peak of the intra-vascular blood. Such light, which is absorbed in the top 0.05 mm of the vessel, can coagulate and thereby thrombose a significant portion of the entire cross section of small vessels (<0.1 mm). Construction of such a pulsed dye laser for dermatology applications has been described previously.

Visible wavelength laser light is less effective on larger diameter vessels (>0.1 mm). The main reason for this is that it is too highly absorbed in blood. Although vessel rupture is possible, this represents a non-optimal mechanism associated with the involvement of only the superficial portion of the vessel, due to the shallow absorption depth of the light. Regrowth of the insufficiently damaged vessels usually occurs under these circumstances. Also, the rupture of the vessel leads to an unsightly post-treatment purpura ('bruising) which can persist for up to 2 weeks. This is not well tolerated by patients.

Figure 2:
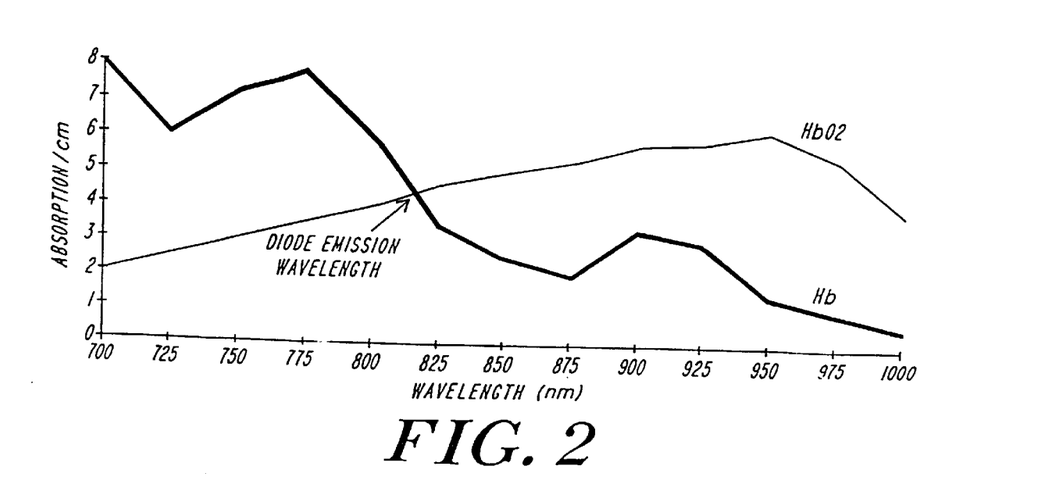

It should be remembered also that dilated vasculature of the extremities is also associated with a different and variable ratio of oxy/deoxygenated hemoglobin, the main absorbing chromophores within the blood. Different considerations are then pertinent in devising an appropriate therapeutic regime. A typical leg vein is characterised by a relatively low oxygenation of around 70%, responsible for an occasional blue 'hue' in some vessels. (Hemoglobin, as typically found in port wine stains on the face, is bright red in color and usually approximates a constant 95–100% oxygenation level). The near infra-red absorption characteristics of the two hemoglobin types which dominate blood absorption are shown in FIG. 2. Both hemoglobin types have equal absorption around 800 nm, rendering absorption independent of chromophore mix (and hence of anatomical location) at this wavelength. This provides a useful insensitivity to anatomical location and individual characteristics in terms of precise level of oxygenation. The magnitude of the absorption coefficient around 810 nm is well suited to the dimensions of the target vessels. Light at this wavelength is absorbed in a 2 mm blood layer, as opposed to light in the historically employed 500–600 nm region, which is absorbed in a blood thickness of less than 200 $\mu$m.

Short wavelengths are also highly scattered as they pass through the turbid dermis to reach the target vessels. An increase in scattering of more than 50% occurs as wavelength is shortened from the near infra-red to the mid-visible. This renders light in the 500–600 nm region less suited to the targeting of deeper dermal vessels.

A further disadvantage associated with existing short wavelength coherent laser sources such as the pulsed dye laser is their short pulsewidth. With a maximum around 1.5 milliseconds, no time for concurrent conduction of the heat is permitted. Further, such an exposure interval is better suited to the thermal relaxation time constants of overlying melanocytes, leading to unwanted temperature rise and the possibility of damage. Such melanocytes have thermal relaxation time constants in the range 100–300 $\mu$secs, and would retain significant thermal energy within a 1.5 millisecond exposure. An available pulsewidth of up to several tens of milliseconds would be desirable and would obviate this effect.

Also, the high cost and the significant bulk of the componentry associated with short wavelength (500–600 nm) coherent light sources are prohibitive factors.

A broadband-emitting incoherent flashlamp light source has been suggested to offer an alternative approach for the treatment of leg veins. Such a source may utilize a spread of principally infra-red wavelengths (550–1200 nm) most of which exhibit a smaller degree of absorption better suited to larger vessels. A longer pulsewidth of up to 100 milliseconds is also available, permitting concurrent heat conduction through the vessel and beyond to a radius of up to 250 $\mu$m. As a consequence, the full volume of the vessels may be affected, as required for vascular necrosis, although significant perivascular necrosis may result.

Clinical results from the use of this class of source are at the preliminary stage and may include a reduction of the hyperpigmentation associated with the shorter wavelength/ pulsewidth dye laser since proximal rupture is no longer the mechanism in effect. Adverse effects include the occurrence of gross heating effects, edema and blistering associated with the incoherent light, since incoherent light has poor penetration characteristics in human tissue. Also, the broad mix of wavelengths includes spectral regions which are less suited to the lesion characteristics, such as the 1000–1200 nm region, which displays little vascular selectivity.

Further, such a system is physically clumsy and difficult to use.

Such an incoherent light cannot be easily focused to a spot size which efficiently overlaps the vessels and hence unaffected tissue is involved in the pathological effects.

The above disadvantages, taken together, limit the applicability of this technology.

Another manifestation of the incoherent flashlamp based light source relates to the use of a mercury-xenon vapor lamp, with specific emission peaks in the visible portion of the spectrum. This incoherent source will often result in gross heating of proximal tissue, with a resultant need for concurrent cooling of the skin. Further, the visible emission spectrum of the lamp lends its use to small vessels found in Port Wine Stains, since the light will be absorbed in the top 0.05 mm of the vessels. Larger leg veins are not cited in the patent for this device for this reason.

Figure 3:
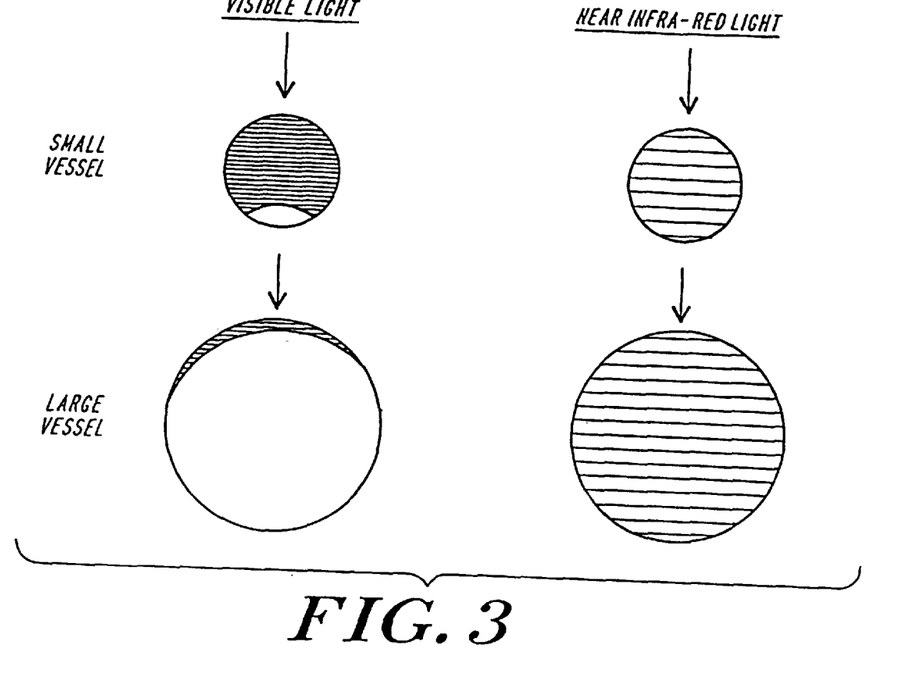

FIG. 3 illustrates graphically the effect of tuned visible (~580 nm) and near infra-red (700–900 nm) coherent light on small (<0.1 mm) and moderate (0.1 mm<diameter<1.0 mm) sized vessels. This figure illustrates the inherent suitability of visible band light to small vessels and of infra-red band light to moderately sized vessels, since destruction of a significant proportion of the vessel is required. This suitability is fully harnessed only if pulse widths of the order of several tens of milliseconds are available, with their concurrent conduction permitting useful proximal vessel wall damage. In particular, the aforementioned pulsewidth of 1.5 milliseconds likely will not permit sufficient conduction of heat to guarantee vascular elimination, since a radius of only 30 $\mu$m is reached in this time. Such a short pulsewidth will further threaten the overlying epidermal layer. Also, extravasation and secondary purpura and hyperpigmentation are likely since efficient coagulation of the intravascular blood and extravascular tissue rim is not attained.

While such short pulses may be appropriate for very small vessels (<100 $\mu$m) which lose heat rapidly, larger vessels are likely to require proportionately longer exposures. Vessels with size in the range 100–500 $\mu$m may require exposure time intervals of 1.5–40 milliseconds, while vessels larger than 500 $\mu$m may require exposure time intervals of 1.5–100 milliseconds.

In FIG. 3, the shading shows the heat generation during the pulse resulting from direct absorption. The denser shading associated with visible light signifies the attainment of high localized temperatures with associated explosive effects. This heat can be expected to conduct further to affect a peri-vascular tissue volume if sufficiently long pulse widths are employed.

A near infra-red narrow-band coherent laser light source with variable pulsewidth would offer the potential for more thorough coagulation of larger vessels, without the adverse effects attendant with the flashlamp source. Such a source intentionally employs wavelengths which exhibit lower blood specificity, contrary to traditional approaches where maximum specificity is sought. Further, such a source would better penetrate to the required depth in tissue than do visible light wavelengths or incoherent infra-red wavelengths, since optical scattering is comensurately reduced. An alternative source of near infra-red light and associated treatment method is described in the following sections.

SUMMARY OF THE INVENTION

The present invention comprises a laser treatment method and apparatus for the removal of vascular and other pigmented lesions from the skin.

The treatment method, according to one embodiment of the invention, includes:

Irradiation of the skin with power level in the range 10–500 Watts, pulsewidth 1–99 milliseconds, and spot size 0.5–10.0 mm with coherent pulsed light with wavelength in the range 700–1000 nm, and fluency in the range of above 100 J/cm² to about 25,200 J/cm², controlling the applied radiation such that desired endpoints are observed during treatment, consisting of mild 'blanching' without significant pigmentary or textural change, allowing the skin to heal for a period of 2–16 weeks, irradiating on 0–5 subsequent occasions with additional exposures, One apparatus for practicing the foregoing embodiment consists of:

a modified high power semiconductor diode laser system with pulsewidth variable from 1–99 milliseconds.

The invention incorporates a modified laser apparatus with new application, together with a novel treatment method for the eradication of leg veins. The new treatment thus developed presents the potential for numerous significant clinical and practical advantages. Clinical advantages include a reduction of unwanted purpura associated with extravasation and to minimization of associated secondary hyperpigmentation. Enhanced clearance will also result from the optimization of wavelength and pulsewidth in a coherent device able to attain significant penetration depth. Pigmented lesions may also be treated with pulses between 1–5 milliseconds. The clinical advantages of the invention are conferred by the use of a 'detuned' coherent infra-red wavelength region and pulsewidth matched to the physical characteristics of the target area. This development of a clinically effective therapeutic treatment using a carefully controlled modified laser apparatus with associated minimization of adverse effects is a major improvement and advance over current options. Other practical advantages include the ease of use of the compact, portable and inexpensive equipment.

DETAILED DESCRIPTION OF THE INVENTION

Theoretical Considerations

As discussed in the foregoing, it is first necessary to identify an optimal wavelength and pulsewidth regime.

In terms of wavelength, a lower absorption coefficient than those exhibited in the visible spectral region is desirable to affect the entire volume of larger vessels. To fill a 1 mm diameter vessel, for example, an absorption coefficient in the range 1–10 cm$^{-1}$ would be optimal, as compared with the absorption coefficient at the yellow wavelength of 585 nm of 300 cm$^{-1}$. As shown in FIG. 2, the near infra-red wavelength range (700–1000 nm) presents absorption coefficients in this range. This graph illustrates the absorption characteristics of oxy and deoxygenated hemoglobin, the dominant blood chromophores.

Figure 4:
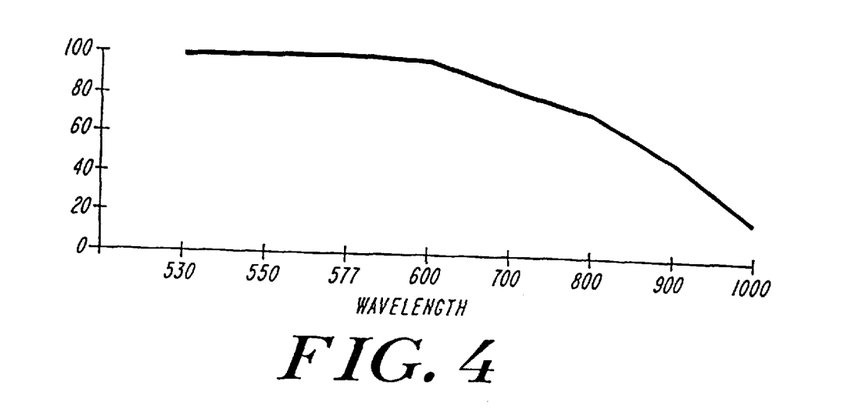

Although the absorption coefficient is significantly less in the near infra-red than that found in the yellow visible region, the thickness of leg vessels is such that the incident energy is effectively utilized throughout the depth of the vessel. Hence, an equivalent proportion of the applied total energy may be absorbed in the vessel in each case, with greater uniformity of deposition for the near infra-red region. This effect, shown in FIG. 4, indicates that the specificity of action is only ultimately lost for wavelengths above 1000 nm, where a significant portion of the light passes through the vessel. In the 530–900 nm spectral region, most of the light is utilized in a 1 mm vessel. For larger vessels in the range 1–2 mm, almost all of such light will be utilized. The precise selection of wavelength determines the uniformity of absorption of the light.

Figure 5:
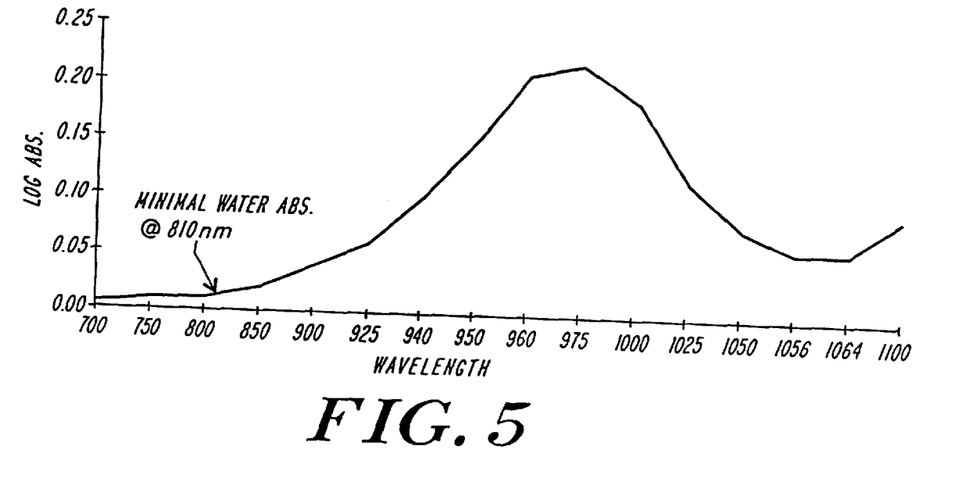

It is also important that tissue water absorption be minimized in order that maximum depth of penetration be attained. Water absorption, shown in FIG. 5, presents a peak at 980 nm and other peaks further into the infra-red. To avoid this broad peak and operate at a reliable wavelength for the laser, a laser source emitting in the 800–850 nm range may be considered optimal. Water absorption at 810 nm, for example, may be considered negligible.

Melanin absorption, still significant at 810 nm, competes for absorption of the light. Significant heating of the epidermis can be avoided by use of pulses or duration longer than several milliseconds. These ensure efficient conduction of the heat from the melanocyte during the pulsed exposure, since melanocytes have thermal relaxation time (time to lose half of their heat) constants of less than 1 millisecond. By comparison, larger blood vessels, which better retain their heat, experience a useful temperature rise. Hence, specificity of vascular effect can be retained.

Conversely, melanocytes may be targeted by means of the use of shorter pulse widths, of around 1–3 milliseconds.

Selection of pulsewidth is of great importance in the precise definition of extent and localization of damage. It is critical that the resultant heat production is unable to conduct widely into the surrounding dermis, since this would cause significant thermal tissue damage. It is however important that a partial conduction occurs. These considerations dictate that the applied pulse duration of the energy be well matched to the mechanical characteristics of the absorbing vessels. For a vessels with size in the range 0.1–3.0 mm, a favorable pulsewidth regime is in the range 1–100 milliseconds, corresponding to a better approximation to the 'thermal relaxation time constant' of the target (time for a vessel to lose half of its heat). In practice, the pulsewidth need not be as long as the thermal relaxation time, but must provide for sufficient lateral conduction to impact a significant perivascular rim of tissue. Since smaller vessels within the above range will more quickly lose their heat, it may be necessary to more rapidly apply the energy to such. Hence, an ideal treatment regime for smaller vessels might use shorter exposure pulse widths within the 1–100 millisecond range than would an ideal regime for larger vessels. This may produce some superficial heating since melanocytes will better retain their heat. Accordingly, as pulsewidth is shortened towards 1 millisecond, it may be appropriate to utilize adjunctive epidermal cooling.

Another useful variation of the treatment parameters involves the application of a number of shorter pulses within the pulse envelope, rather than a continuous longer exposure. This allows some vascular relaxation during the exposure which may create better uniformity of the heating process.

To further validate this thought process, a computer technique known as Monte-Carlo modeling may be undertaken to simulate the effect of such laser light on leg veins. This intensive approach generates many millions of optical events in the skin to ultimately derive optical energy distributions. In this modeling, a sample 0.5 mm thick blood layer was assumed at a 0.5 mm depth beneath a highly scattering epidermal/dermal top layer. This model yields an optical distribution which may be converted to a thermal distribution by means of the calculations below.

$$\S T = E/C \times M$$

where $\S T$=temperature rise in small tissue segment

E=energy deposited in tissue segment=no. of photons× photon energy

C=specific heat capacity of tissue

M=mass of tissue segment.

Tissue parameters, such as scattering and absorption, as used in this model were obtained from the literature, although it should be noted that no previous modeling work is evident which addresses the treatment of leg veins in the wavelength region described here.

Figure 6:
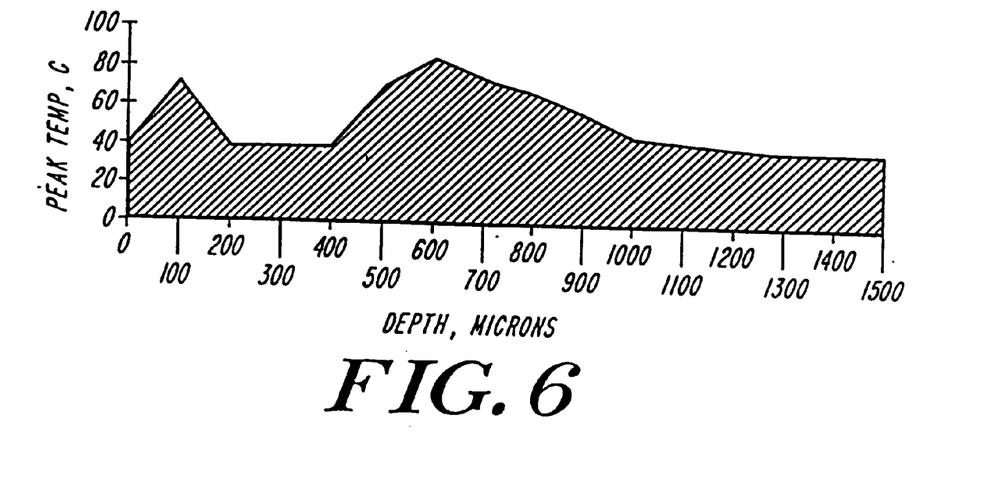

Various power and energy levels were used in the modeling. As an example, FIG. 6 illustrates the thermal profile at the end of an exposure of 20 Watts of 800 nm laser light at this wavelength. Various beam spot sizes and pulse widths were modeled. In FIG. 6, a spot size of 1 mm, combined with a pulsewidth of 30 milliseconds, were employed (note that the blood vessel surface begins at a depth of 500 um). The temperatures shown are sustained in the blood vessel beyond the duration of the exposure (30 milliseconds), providing sufficient locally deposited energy to kill the vessel. The thin epidermal layer loses heat more rapidly and is thereby spared from gross damage for such a long pulsewidth. Minimal perivascular heating is expected for appropriate pulse durations (1–100 milliseconds).

This figure illustrates that, while light in the 800–850 nm region has relatively low absorption, a preferential effect on the vasculature may still be induced.

From the above theoretical studies, it has become apparent that a laser source emitting in the wavelength region 800–850 nm. with variable pulsewidth and spot size capabilities, will meet the conditions required for optimal clinical treatment of a sample leg vessel with diameter of 0.5 mm. The same principles apply to a range of vessel size between 0.1–3.0 mm diameter. It is important that the source be a laser, with its attendant coherence, rather than an incoherent source such as, for instance, a flashlamp-based source. Coherent light is unidirectional in nature and better suited to penetration through turbulent human tissue.

In the modeling example cited above, as stated, a vessel of diameter 0.5 mm at depth 0.5 mm was brought to damage threshold by means of a 20 Watt source with 1.0 mm spot size, operating with a pulsewidth of 30 milliseconds. To allow for deeper, thicker vessels, and for the use of longer pulse widths and larger round and elliptical spot sizes up to 10 mm, I have calculated that a peak power of up to 500 Watts may be required. An associated pulsewidth in the range 1–99 milliseconds would be required.

By means of the use of such an apparatus, adverse sequelae associated with currently available technologies will be reduced. In particular, purpura and post-treatment hyperpigmentation associated with mechanical rupture and extra-vasation will be greatly reduced, as the longer pulse widths produce a more uniform effect. Also, deeper penetration of the long coherent 800 nm wavelength will improve treatment efficacy.

The above represents a summary of the theoretical considerations employed to calculate an appropriate parameter set. As part of this invention, an appropriate apparatus and treatment method were also devised.

Apparatus

It was determined after a review of the scientific literature, that some manifestation of modified diode laser technology would be capable of providing the requisite parameter set.

Semiconductor diode laser technology, first developed in 1962, today finds application in devices ranging from consumer electronics and communications to medicine.

A basic system, in the high power configuration envisaged here, consists of an electronic power supply coupled to a semiconductor crystal encapsulated in an optical chamber capable of capturing and harnessing optical emissions from the crystal. When a large direct current is passed through the crystal, optical emission is generated and amplified. A beam of light results, with a high degree of brightness and directionality.

The basic system is further refined by means of the addition of thermo-electric cooling circuitry for temperature stabilization and of electronic circuitry for exposure control and pulsewidth generation. Maintenance needs are minimal with a 5000+ hour life on the sources equating to several years of use. This low maintenance feature recommends the technology to the busy surgical suite.

Individual diode elements have limited output power capability and beam shapes which are not amenable to ease of delivery to distant sites. Recent efforts have concentrated on beam shaping and combination of beams from a plurality of single elements. Each single element can deliver up to 1 Watt of CW power.

As a consequence, by means of the combination of beams from many such elements on diode bars, it is now possible to deliver tens of watts of diode laser light through flexible fiber optical cable to a distant site. These high power levels as recently demonstrated by other inventors (up to 100 Watts) have made possible the new treatment concept outlined previously, in which such a source, appropriately modified, may be used for the current application.

A number of medical device companies have packaged diode laser systems for medical use, based on the above OEM subcomponents. Use of their finished systems is advocated for urology, gynecology, general and plastic surgery, gastroenterology and ENT. None of these applications are directly vascular in nature. Some ophthalmic applications have also been studied in which small retinal vessels were treated with a lower power (up to 1.3 Watts) diode laser. It has been shown that small vessels (<200 um) could be coagulated, but that optimal use would entail the use of an adjunctive sensitizer dye such as indocyanine green. Larger vessels were not studied. No direct vascular use of the diode laser in Dermatology has been studied at this time.

Diode laser systems as described above have been utilized for general surgical applications on soft tissue, whereby a non-specific cutting action results from the delivery of long pulses of light (>100 milliseconds pulse widths are typically available from the devices), with power levels in the range 10–60 Watts. In this mode, such a device acts as an optical scalpel, with some associated coagulative potential.

One embodiment of the invention involves the modification of such a system by means of electronic control circuitry to obtain shorter pulsewidth (1–99 millisecond) operation for specific use in selective dermatological surgery. Such an embodiment may be further modified by the optimization of the internal semiconductor array design for pulsed operation and for higher power density focusing of the light. This may be achieved by judicious coating of the individual diode facets and closer placement of the diode elements within the array than is typical in an array optimized for Continuous Wave operation. A higher power density may thereby be realized from the array.

The practice of the invention harnesses the specific targeting potential of the device by means of a careful control and administration of the parameters as modeled previously. By this means, light is to pass through overlying tissue, affecting only the desired target vessels.

Direct targeting of large blood vessels on the legs with a high power (~10–500 Watts) and short pulsewidth diode source has never previously been reported.

The invention consists of a clinical treatment methodology for the eradication of unwanted leg vessels, described in the next section. Pigmented lesions of the skin may be similarly treated, and require the use of shorted pulsewidth. The treatment method employs modified specific optical apparatus which is described in this section in terms of preferred and alternative embodiments. The combination of parameters described below under 'preferred specification' have not so far been reported in Dermatology and may not have been used in any other medical specialty.

One preferred specification for the device is listed below:

Host material: GaAs semiconductor laser source wavelength range: 800–850 nm pulsewidth: 1–99 milliseconds power level: 10–300 Watt, 1 Watt increments repetition rate: 1–20 Hz.

spot size on skin: 0.5–10 mm, variable delivery system: fiber, with dermatology handpiece termination laser cooling method: thermoelectric pulsing method: electrical aiming beam: red diode or helium neon laser (1–10 mW)

tissue cooling: optional, may be required for 1–3 millisecond pulses

This preferred embodiment can specifically be utilized for the treatment of leg vessels and may also find application in the treatment of facial telangiectasia, pigment removal and other Dermatological conditions requiring high selectivity.

A second embodiment utilizes a commercial scanner to simulate a larger spot size or cover a larger treatment area with greater uniformity. This scanner would replace the standard handpiece and would serve to contiguously place treatment spots on the skin. This would allow for the use of a smaller incident spot size with consequent higher power density, yet still permit the treatment of large vessels up to 3 mm. Alternatively, this would allow for the rapid uniform coverage of large treatment areas with any particular spot size. Scan area would range from as little as 2 mm$^2$ to as much as 10,000 mm$^2$.

A third alternative embodiment employs the use of a contrasting dye such as Indocyanine Green, which enhances absorption in the preferred wavelength region. This would be injected into the patient prior to treatment with the diode laser, in order to enhance the selectivity of the laser action.

A fourth alternative embodiment utilizes a different semiconductor material variant producing a wavelength in the range 850–1000 nm, with a power level in the range 10–500 Watts.

A fifth alternative embodiment utilizes a second host material 'pumped' by the diode laser. This host material, which itself would then lase at a different wavelength, might consist of a polymer encapsulated dye material, or some other glass or crystal structure doped with lasing ions.

All of the envisaged embodiments produce near infra-red light with pulse widths and power levels amenable to the treatment of the targeted leg vessels as calculated previously.

Figure 7:
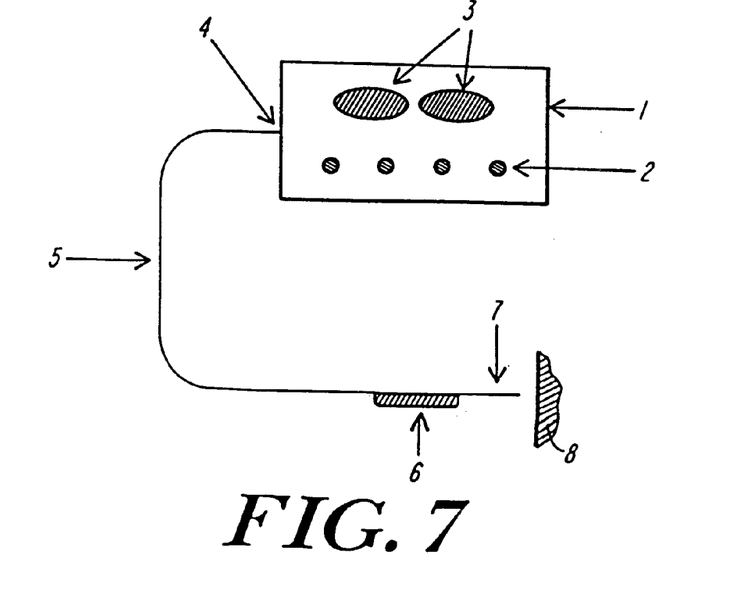

This first preferred embodiment is sketched as FIG. 7:

In practice, a separate foot switch (not shown) provides triggering to the laser source found within the laser head cabinetry (1). The source consists of a set of arrays of individual laser diodes. Light from these diodes is typically collected in a series of individual small diameter fibers constituting a bundle. This bundle is grouped together physically within the cabinetry enclosure and light coupled via a high efficiency connector into a single larger diameter fiber. An external connector (4) provides an interface to an external length of optical fiber or light guide (5). This optical delivery media is then coupled into a handpiece (6) containing focusing lenses. These lenses, together with a distance gauge (7), provide precise positioning and laser beam placement onto the patient's skin (8). The beam at the treatment site may be focused or may be converging, to achieve a better penetration within the tissue. Power level, repetition rate, and pulsewidth of the source are controlled by means of the electronic controls (2) which together provide access to the specification set listed previously. Displays (3) permit verification of the selected parameter set.

An incorporated visible 'aiming beam', within the cabinetry enclosure also delivered through the light guide, provides verification of the ultimate placement of the invisible treatment laser spot. An audible tone sounds when the short pulses are being administered to provide the physician with additional feedback.

An optional external cooling apparatus may be employed when short pulses (1–3 milliseconds) are being used for the treatment of vascular lesions. This would employ the application of a chilled media which would reduce epidermal temperature by up to 20° C. to lower its damage threshold.

Clinical Treatment Methodology

The goal of the treatment is to lighten and eventually clear the vessel while leaving the surrounding normal skin intact and unaffected. Below is presented an optimal and novel therapeutic treatment methodology suitable for use in a variety of different clinical applications.

Dermatological Applications and Uses (i) Telangiectasia of the legs (ii) Mature vascular lesions of the head and neck, including Port wine stains and telangiectasia (ii) Epidermal and dermal pigment removal A number of major advantages and conveniences are provided by the present treatment method, including:

1. The present methodology envisages the use of a specific parameter set chosen to provide optimum selectivity of damage to the target tissue only. The epidermis and peri-vascular dermis are spared while damage is administered, in a controlled fashion, uniformly throughout the targeted vessels or pigmented structures.

2. The vessels are uniformly coagulated rather than mechanically ruptured. This means that blood does not leak out of the vessels into the surrounding tissue. This leakage is responsible for the gross, and persistent, purpura and hyperpigmentation which is cosmetically troublesome to the patient. The present invention should minimize these risks.

3. The invention provides for the use of narrow-band coherent infra-red light. Such light is able to penetrate deep into the dermis with minimal scattering or competitive absorption and affect most of the visible vasculature.

4. The equipment used to provide the therapy can be manufactured at relatively low cost and has great case of portability. This will ultimately result in greater patient access to the therapy.

5. The procedure is relatively gentle and painless, and obviates the use of multiple needle injections as associated, for instance, with sclerotherapy.

6. Several treatments are required. Each treatment will provide an occasion for the physician to tailor the parameters to the individual needs of the patient. Hence, the personal health, safety and cosmetic appearance of the skin are affected only to the extent required, and any side effects minimized.

7. Minimal damage is caused to surrounding skin structures, which do not absorb well at the near- infra-red wavelengths. Water absorption is low, minimizing peri-vascular direct heating, and epidermal heating is low, minimizing epidermal pigmentary change and epidermal disruption. This is turn minimizes any complications associated with wound formation.

General Treatment Procedures and Preferred Details

Vessels with size in the range 0.1–3.0 mm will respond best to treatment. Vessels with a powerful deep feeder vein are least likely to respond to treatment by any available method.

A power level in the range 10–500 Watts is used, with 40–50 Watts being a 'typical' value for a small associated spot size of 1 mm. Larger spot sizes up to 10 mm will require higher power. A Pulsewidth in the range of 1–99 milliseconds will be used, with smaller vessels requiring somewhat shorter exposure pulse widths. Use of the shortest pulse widths (1–3 milliseconds) may require the adjunctive cooling of the epidermis. A wavelength in the range 800–850 nm is preferred due to its insensitivity to blood oxygenation. This removes an important variable from clinical consideration.

After treatment, the site may be somewhat blanched (whitened) due to some coagulation of tissue. Some fine purpura may also be present, as a result of the intra-vascular coagulated blood or vasculitis associated with vascular swelling.

Compression may be applied to the site pursuant to treatment to minimize the potential of the body to 're-grow' the endothelial cell structures defining the vessels.

An assessment will be made at the second visit relating to any color or texture change of the skin. The vessel itself will also be graded for any lightening. Absence of any lightening or adverse effects will be taken as indicative of the need to increase energy or exposure time.

Occurrence of significant adverse sequellae will be taken as indicative of the need to decrease power and exposure parameters.

Detailed Protocol

The vessel group to be treated is photographed under controlled conditions and its diameter measured using a slide scale or needle. It is further examined to detect the presence of scarring or otherwise abnormal color or texture.

The site of treatment is first shaved, to remove obstructive absorbing hairs.

Individual vessels are designated as test sites to which different carefully chosen parameters of laser light are applied. An initial set of parameters for smaller vessels (0.1–0.5 mm) might be: 40–50 Watts of light, 1 mm spot size, 3–20 millisecond exposure time. Larger vessels may respond better to somewhat longer pulse widths and may best be treated with larger spot size. This may in turn require the use of higher power up to 500 Watts. Several such spots would be placed linearly along one of the vessels comprising the test site. Different vessels within the group are exposed with increasing power levels or pulse durations. Increases may be in steps of 5 Watts and 3–5 milliseconds. Feedback is obtained from each application in terms of immediate tissue response and used to determine subsequent test site parameters. Desired response includes a whitening of the vessel without abnormal texture or damage to the overlying tissue. Some reddening of the treated area is also desirable, which is associated with the inflammatory (erythemic) response of the body.

Following treatment, a topical antibiotic ointment may be applied to the treated site and the skin area covered with a dressing. This dressing, or a separate structure, may also be used to achieve localized compression and restriction of blood flow.

The patient will return after a specified healing period (usually 2–16 weeks) for evaluation and further treatment. These additional treatments (typically up to 5) will be administered with the parameters found to induce optimal vessel lightening with minimal adverse sequellae. Parameters will be adjusted if the response is inadequate (insufficient lightening) or too severe (induration, ulceration or pigmentary change to the overlying epidermis). In the former case, applied power and/or pulsewidth will be increased, while in the latter a decrease will be effected.

If a vessel does not respond after a total of 6 treatments, treatment should be discontinued. This is likely to be indicative of the presence of a high pressure underlying feeder vein system, or some other combination of adverse mechanical or biological characteristics. In any event, the patient should be followed for up to one year to note any incidence of recurrence.

I claim:

1. A laser treatment method for removal of unwanted leg veins and other vascular lesions from skin of a human, said method comprising the steps of:

irradiating on a first occasion a chosen treatment site with a pulsed coherent light, at an exposure spot size of about 0.5–1.0 mm, said treatment site containing vessels having a diameter of about 0.1 to 3.0 mm, said light having:
a wavelength in the range of about 700–1000 nm said light having;
a power level in the range of about 40–5000 Watts;
a pulse duration in the range of about 20–99 milliseconds; and
a fluency in the range of above 100 J/cm$^2$ to about 25,200 J/cm$^2$;

allowing the skin to heal for a time period of about 2–16 weeks; and irradiating on about 1–5 subsequent occasions each vessel previously treated with said light in said wavelength, power level and pulse duration ranges.

2. The laser treatment method recited in claim 1, further comprising the step of shaving said treatment site.

3. The laser treatment method recited in claim 1, wherein said light has the wavelength of 800–850 nm.

4. The laser treatment method recited in claim 1, wherein said irradiation on the first occasion employs a greater total energy application than on subsequent occasions.

5. The laser treatment method recited in claim 1, wherein said irradiation on the first occasion employs a lesser total energy application than on subsequent occasions.

6. The laser treatment method recited in claim 1, further comprising the step of applying local compression pursuant to treatment to limit potential for recanalization of said treatment site.

7. The laser treatment method recited in claim 1, whereby a sensitizing dye, such as indocyanine green, is first injected into a local venous system.

8. The laser treatment method recited in claim 1, whereby the steps of irradiating further comprise applying short pulsed laser light to treat pigmented lesions and marks of the skin.

9. The laser treatment method recited in claim 1, whereby a plurality of short pulses in a range of 1–3 milliseconds are used with adjunctive cooling to treat vascular lesions.

10. The laser treatment method as recited in claim 1, wherein said light comprises at least one pulse envelope, each envelope containing a train of pulses.

11. A therapeutic treatment device for removal of unwanted leg veins and other vascular lesions from skin of a human, said device, comprising:
- a laser head containing a power source, laser source, controls, and cooling electronics;
- an optical fiber connector and light guide optically coupled to the laser head for receiving light produced by the laser head;
- a dermatology handpiece and a focusing optics element and a distance gauge for distance control of tissue contact, connected to the optical fiber; and
- a control circuitry element electronically connected to and controlling generation of a plurality of pulse widths in a pulsewidth duration in the range of about 1–99 milliseconds to obtain fluencies in the range of above 100 J/cm$^2$ to about 25,200 J/cm$^2$.

12. The therapeutic treatment device of claim 11, wherein the laser source is a semiconductor laser operating with a wavelength range of 800–850 nm, and inter-element spacing, facet coating and collection optics of the laser source diode arrays and collection optics are selected to provide short pulsed high peak power operation in the pulsewidth range of 1–100 millisecond.

13. The therapeutic treatment device of claim 11, wherein the laser is a semiconductor laser with modified control circuitry allowing for pulsewidth controllability in the pulsewidth range of 1–99 milliseconds.

14. The therapeutic treatment device of claim 11, whereby the laser source is adapted for total power emission in a power range of 10–500 Watts; pulsewidth variability in the pulsewidth range of 1–99 milliseconds and wavelength variability in the wavelength range of 700–1000 nm.

15. The therapeutic treatment device of claim 11, wherein the device has the capability of focusing or converging a treatment site within the skin to provide for better penetration in tissue and reduced epidermal fluence.

16. The device of claim 11, wherein the laser source further comprises a diode laser pumped material such as dye-impregnated polymer or active ion doped glass or crystal host.

17. A therapeutic treatment device for removal of unwanted leg veins and other vascular lesions from skin of a human, said device, comprising:
- a laser head containing a power source, a laser source, a plurality of controls, and a cooling electronics element;
- an optical fiber connector and light guide optically coupled to the laser head for receiving light produced by the laser head;
- a dermatology handpiece and distance gauge for distance control of tissue contact, connected to the optical fiber; and
- a control circuitry element electronically connected to and controlling generation of a plurality of pulsewidths in a pulsewidth range of 1–99 milliseconds to obtain fluencies in the range of above 100 J/cm$^2$ to about 25,200 J/cm$^2$.

18. The device of claim 17, wherein the laser source is a semiconductor laser operating with a wavelength range of 800–850 nm.

19. The therapeutic treatment device of claim 17, wherein the laser source is a semiconductor laser.

20. The therapeutic treatment device of claim 17, wherein the laser source is adapted for a total power emission of 10–60 Watts and wavelength range of 700–1000 nm.

21. The device of claim 17, wherein the laser source consists of a diode laser pumped material such as dye-impregnated polymer or active ion doped glass or crystal host.

* * * * *